United States Patent
Friedman et al.

(10) Patent No.: US 12,011,457 B2
(45) Date of Patent: *Jun. 18, 2024

(54) SELENIUM DISULFIDE COMPOSITIONS FOR USE IN TREATING MEIBOMIAN GLAND DYSFUNCTION

(71) Applicant: Azura Ophthalmics Ltd., Tel Aviv (IL)

(72) Inventors: Doron Friedman, Carme-Yosrf (IL); Yair Alster, Tel Aviv (IL); Omer Rafaeli, Udim (IL); Shimon Amselem, Rehovot (IL); Zakhar Nudelman, Netanya (IL)

(73) Assignee: AZURA OPHTHALMICS LTD, Tel Aviv (IL)

( * ) Notice: Subject to any disclaimer, the term of this patent is extended or adjusted under 35 U.S.C. 154(b) by 72 days.

This patent is subject to a terminal disclaimer.

(21) Appl. No.: 17/320,731

(22) Filed: May 14, 2021

(65) Prior Publication Data

US 2021/0330703 A1 Oct. 28, 2021

Related U.S. Application Data

(63) Continuation of application No. 16/093,615, filed as application No. PCT/IB2017/000542 on Apr. 13, 2017, now Pat. No. 11,040,062.

(60) Provisional application No. 62/322,627, filed on Apr. 14, 2016.

(51) Int. Cl.

| *A61K 33/04* | (2006.01) |
| *A61K 9/00* | (2006.01) |
| *A61K 9/06* | (2006.01) |
| *A61K 9/16* | (2006.01) |
| *A61K 47/06* | (2006.01) |
| *A61K 47/44* | (2017.01) |

(52) U.S. Cl.
CPC ............ *A61K 33/04* (2013.01); *A61K 9/0048* (2013.01); *A61K 9/06* (2013.01); *A61K 9/16* (2013.01); *A61K 47/06* (2013.01); *A61K 47/44* (2013.01)

(58) Field of Classification Search
CPC ........ A61K 33/04; A61K 9/0048; A61K 9/06; A61K 9/16; A61K 47/06; A61K 47/44
See application file for complete search history.

(56) References Cited

U.S. PATENT DOCUMENTS

| 3,236,730 A | 2/1966 | Galin |
| 5,645,827 A | 7/1997 | Marlin et al. |
| 5,798,121 A | 8/1998 | Cauwet et al. |
| 6,153,607 A | 11/2000 | Pflugfelder et al. |
| 6,348,508 B1 | 2/2002 | Denick, Jr. et al. |
| 7,288,259 B2 | 10/2007 | Sanders et al. |
| 8,420,699 B1 | 4/2013 | Dubow |
| 8,449,928 B2 | 5/2013 | Gilbard et al. |
| 8,455,016 B2 | 6/2013 | Maskin |
| 9,463,201 B2 | 10/2016 | Alster et al. |
| 10,034,887 B2 | 7/2018 | Alster et al. |
| 10,588,915 B2 | 3/2020 | Alster et al. |
| 10,688,122 B2 | 6/2020 | Amselem et al. |
| 10,772,899 B2 | 9/2020 | Alster et al. |
| 11,013,749 B2 | 5/2021 | Alster et al. |
| 11,040,062 B2 | 6/2021 | Friedman et al. |
| 11,324,775 B2 | 5/2022 | Bosworth et al. |
| 2003/0228299 A1 | 12/2003 | Droy-Lefaix et al. |
| 2004/0171561 A1 | 9/2004 | Popp |
| 2004/0192647 A1 | 9/2004 | Babizhayev |
| 2005/0124690 A1 | 6/2005 | Yoon et al. |
| 2005/0197614 A1 | 9/2005 | Pritchard et al. |
| 2006/0188471 A1 | 8/2006 | Podolsky et al. |
| 2007/0082017 A1 | 4/2007 | Tseng et al. |
| 2007/0104758 A1 | 5/2007 | Hamilton et al. |
| 2007/0166402 A1 | 7/2007 | Friedlaender et al. |
| 2007/0269537 A1 | 11/2007 | Gupta |
| 2007/0280924 A1 | 12/2007 | Daniels et al. |
| 2008/0020044 A1 | 1/2008 | Alam et al. |
| 2008/0081996 A1 | 4/2008 | Grenon et al. |
| 2008/0103376 A1 | 5/2008 | Felder |
| 2008/0242729 A1 | 10/2008 | Bollag |
| 2009/0123527 A1 | 5/2009 | Alam et al. |
| 2009/0214676 A1 | 8/2009 | Gao et al. |
| 2009/0238810 A1 | 9/2009 | Nyunt |
| 2010/0034870 A1 | 2/2010 | Sim et al. |
| 2010/0204317 A1 | 8/2010 | Hunt et al. |
| 2010/0256552 A1 | 10/2010 | Korb et al. |
| 2010/0285155 A1 | 11/2010 | Gilbard et al. |
| 2011/0022010 A1 | 1/2011 | Grenon et al. |

(Continued)

FOREIGN PATENT DOCUMENTS

| CN | 1093897 A | 10/1994 |
| CN | 101612161 A | 12/2009 |

(Continued)

OTHER PUBLICATIONS

Akyol-Salman et al. Efficacy of topical N-acetylcysteine in the treatment of meibomian gland dysfunction. J Ocul Pharmacol Ther 26(4):329-333 (2010).

Barrault et al. Immortalized sebocytes can spontaneously differentiate into a sebaceous-like phenotype when cultured as a 3D epithelium. Exp Dermatol 21:299-319 (2012).

Butovich et al. Human tear film and meibum. Very long chain wax esters and (O-acyl)-omega-hydroxy fatty acids of meibum. J Lipid Res 50(12):2471-2485 (2009).

(Continued)

*Primary Examiner* — Shirley V Gembeh
(74) *Attorney, Agent, or Firm* — WILSON SONSINI GOODRICH & ROSATI

(57) ABSTRACT

Described herein are compositions and methods for the treatment of meibomian gland dysfunction. Said methods are performed by administering said composition comprising a selenium disulfide and an anhydrous semi-solid base. The stable anhydrous composition are substantially free of selenium disulfide agglomerates.

27 Claims, 2 Drawing Sheets

(56) References Cited

U.S. PATENT DOCUMENTS

| | | |
|---|---|---|
| 2011/0059925 A1 | 3/2011 | Donnenfeld |
| 2011/0104206 A1 | 5/2011 | Nanduri et al. |
| 2011/0124725 A1 | 5/2011 | Maskin |
| 2011/0130729 A1 | 6/2011 | Korb et al. |
| 2011/0137214 A1 | 6/2011 | Korb et al. |
| 2011/0294897 A1 | 12/2011 | Aberg et al. |
| 2012/0016275 A1 | 1/2012 | Korb et al. |
| 2012/0028929 A1 | 2/2012 | Power et al. |
| 2012/0093876 A1 | 4/2012 | Ousler, III et al. |
| 2012/0128763 A1 | 5/2012 | Maskin |
| 2012/0190661 A1 | 7/2012 | Trogden et al. |
| 2012/0226156 A1 | 9/2012 | Grenon et al. |
| 2012/0264681 A1 | 10/2012 | Braiman-Wiksman et al. |
| 2012/0288575 A1 | 11/2012 | Gilbard et al. |
| 2013/0053733 A1 | 2/2013 | Korb et al. |
| 2013/0131171 A1 | 5/2013 | Maskin |
| 2013/0184242 A1 | 7/2013 | Eini et al. |
| 2013/0224272 A1 | 8/2013 | Gao et al. |
| 2013/0274214 A1 | 10/2013 | Brubaker |
| 2013/0280340 A1 | 10/2013 | Dobbie |
| 2013/0281390 A1 | 10/2013 | Brubaker |
| 2013/0331768 A1 | 12/2013 | Nichamin |
| 2013/0344128 A1 | 12/2013 | Gao et al. |
| 2013/0345185 A1 | 12/2013 | Mitra et al. |
| 2014/0005171 A1 | 1/2014 | Aukunuru et al. |
| 2014/0017886 A1 | 1/2014 | Teo et al. |
| 2014/0058340 A1 | 2/2014 | Guillon et al. |
| 2014/0142055 A1 | 5/2014 | Hosseini et al. |
| 2014/0142668 A1 | 5/2014 | Guillon et al. |
| 2014/0154333 A1 | 6/2014 | Moloney |
| 2014/0171886 A1 | 6/2014 | Ogawa et al. |
| 2014/0206708 A1 | 7/2014 | Ren et al. |
| 2015/0080349 A1 | 3/2015 | Blackwell et al. |
| 2015/0265565 A1 | 9/2015 | O'Haimhirgin |
| 2017/0035785 A1 | 2/2017 | Alster et al. |
| 2017/0087179 A1 | 3/2017 | Amselem et al. |
| 2017/0312364 A1 | 11/2017 | Bossy et al. |
| 2018/0043024 A1 | 2/2018 | Sakurai et al. |
| 2018/0177391 A1 | 6/2018 | Korb et al. |
| 2020/0179440 A1 | 6/2020 | Amselem et al. |
| 2021/0236518 A1 | 8/2021 | Alster et al. |
| 2022/0226367 A1 | 7/2022 | Amselem et al. |
| 2023/0218642 A1 | 7/2023 | Alster et al. |

FOREIGN PATENT DOCUMENTS

| | | |
|---|---|---|
| CN | 102038953 A | 5/2011 |
| CN | 103002737 A | 3/2013 |
| CN | 103037802 A | 4/2013 |
| CN | 105456287 A | 4/2016 |
| EP | 0930072 A1 | 7/1999 |
| EP | 1621191 A1 | 2/2006 |
| EP | 1915998 A1 | 4/2008 |
| EP | 2633852 A1 | 9/2013 |
| EP | 2664330 A1 | 11/2013 |
| EP | 2667877 A2 | 12/2013 |
| EP | 3206497 A1 | 8/2017 |
| JP | H07233057 A | 9/1995 |
| JP | H11292793 A | 10/1999 |
| JP | 2010510961 A | 4/2010 |
| JP | 2010520210 A | 6/2010 |
| JP | 2014518275 A | 7/2014 |
| JP | 2015514722 A | 5/2015 |
| WO | WO-9611686 A1 | 4/1996 |
| WO | WO-9724116 A2 | 7/1997 |
| WO | WO-03035076 A1 | 5/2003 |
| WO | WO-03050190 A2 | 6/2003 |
| WO | WO-2005067892 A1 | 7/2005 |
| WO | WO-2006137426 A1 | 12/2006 |
| WO | WO-2007070463 A2 | 6/2007 |
| WO | WO-2007133703 A2 | 11/2007 |
| WO | WO-2008027069 A1 | 3/2008 |
| WO | WO-2008068866 A1 | 6/2008 |
| WO | WO-2008106228 A2 | 9/2008 |
| WO | WO-2010006117 A2 | 1/2010 |
| WO | WO-2011006079 A2 | 1/2011 |
| WO | WO-2012092320 A2 | 7/2012 |
| WO | WO-2012155062 A1 | 11/2012 |
| WO | WO-2012161112 A1 | 11/2012 |
| WO | WO-2013003731 A2 | 1/2013 |
| WO | WO-2014078956 A1 | 5/2014 |
| WO | WO-2015017316 A2 | 2/2015 |
| WO | WO-2015022546 A1 | 2/2015 |
| WO | WO-2015169728 A1 | 11/2015 |
| WO | WO-2016063130 A1 | 4/2016 |
| WO | WO-2017055924 A2 | 4/2017 |
| WO | WO-2017178892 A2 | 10/2017 |
| WO | WO-2017182885 A2 | 10/2017 |
| WO | WO-2020208418 A1 | 10/2020 |

OTHER PUBLICATIONS

Chew et al. An instrument for quantifying meibomian lipid on the lid margin: the Meibometer. Curr Eye Res 12(3):247-254 (1993).

Driver et al. Meibomian Gland Dysfunction. Survey of Ophthalmology 40(5):343-367 (1996).

Geerling G., et al., The International Workshop on Meibomian Gland Dysfunction: Report of the Subcommittee on Management and Treatment of Meibomian Gland Dysfunction. The Association for Research in Vision and Ophthalmology, Inc., IOVS Special Issue 2011, 52.4 (2011): 2050-2064.

Heiligenhaus et al. Therapy of dry eye disorders [Therapie von Benetzungsstorungen]. Klin Monatsbl Augenheilkd 204:162-168 (1994) (English Summary).

Itoh et al. The Molecular Mechanism of the Synthesis of the 21st Amino Acid, Selenocysteine. Journal of Japanese Crystal Society 56(3):186-193 (2014) (English Abstract).

Knop et al. The International Workshop on Meibomian Gland Dysfunction: Report of the Subcommittee on Anatomy, Physiology, and Pathophysiology of the Meibomian Gland. IOVS 52(4):1938-1978 (2011).

Koenig et al. Organic Sulfur Derivatives. V.2 Preparation and Properties of Some Long-Chain Mercapto Acids and Related Compounds. J Org Chem 23:1525-1530 (1958).

Maskin. Intraductal meibomian gland probing relieves symptoms of obstructive meibomian gland dysfunction. Cornea 29(10):1145-1152 (2010).

Millar et al. The effect of dietary and pharmacological manipulation of lipid production in the Meibomian and Harderian glands of the rabbit. Lacrimal Gland, Tear Film, and Dry Eye Syndromes 3. Advances in Experimental Medicine and Biology 506:431-440 (2002).

Nagymihalyi et al. The influence of eyelid temperature on the delivery of Meibomian oil. Exp Eye Res 78:367-370 (2004).

Nederfors et al. Effects of the antihypertensive drug captopril on human salivary secretion rate and composition. Eur J Oral Sci 103(6):351-354 (Dec. 1995) (Abstract).

Nelson et al. The International Workshop on Meibomian Gland Dysfunction: Report of the Definition and Classification Subcommittee. Invest Ophthalmol Vis Sci. 52(4):1930-1937 (2011).

Nichols. The International Workshop on Meibomian Gland Dysfunction: Introduction. Invest Ophthalmol Vis Sci 52(4):1917-1921 (2011).

PCT/IB2015/02164 International Search Report and Written Opinion dated Mar. 29, 2016.

PCT/IB2017/00542 International Search Report and Written Opinion dated Sep. 21, 2017.

PCT/US2016/01510 International Search Report and Written Opinion dated May 24, 2017.

Qiao et al. Emerging treatment options for meibomian gland dysfunction. Clinical Ophthalmology 7:1797-1803 (2013).

Seifert et al. Immunocytochemical and ultrastructure evaluation of the distribution of nervous tissue and neuropeptides in meibomian gland. Graefe's Arch Clin Exp Ophthalmol 234:648-656 (1996).

U.S. Appl. No. 14/732,622 Office Action dated Nov. 19, 2015.
U.S. Appl. No. 15/269,833 Office Action dated Aug. 7, 2017.
U.S. Appl. No. 15/269,833 Office Action dated Jan. 11, 2017.
U.S. Appl. No. 15/279,301 Office Action dated Apr. 25, 2019.

(56) References Cited

OTHER PUBLICATIONS

U.S. Appl. No. 15/279,301 Office Action dated Aug. 31, 2017.
U.S. Appl. No. 15/279,301 Office Action dated Mar. 14, 2018.
U.S. Appl. No. 15/279,301 Office Action dated Mar. 29, 2017.
U.S. Appl. No. 15/279,301 Office Action dated Nov. 27, 2018.
U.S. Appl. No. 16/019,253 Office Action dated May 16, 2019.
U.S. Appl. No. 16/093,615 Office Action dated Dec. 22, 2020.
U.S. Appl. No. 16/093,615 Office Action dated Jul. 6, 2020.
U.S. Appl. No. 16/562,374 Office Action dated Oct. 30, 2019.
U.S. Appl. No. 16/919,749 Office Action dated Oct. 5, 2020.
U.S. Appl. No. 16/795,497 Office Action dated Jul. 29, 2021.
Wong et al. Selenium (Selsun) in the Treatment of Marginal Blepharitis. AMA Arch Ophthalmol 55(2):246-253 (1956).
Anonymous. Ointments and Types of ointment bases. Pharmaceutical Drugs and Dosage: Semisolid dosage forms. Available at https://www.pharmacy180.com/article/ointments-and-types-of-ointment-bases-2856/ (2019).
U.S. Appl. No. 17/236,258 Office Action dated Oct. 18, 2022.
De Villiers. Chapter 23: Ointment Base. A Practical Guide to Contemporary Pharmacy Practice. Publisher: Wolters Kluwer Health/Lippincott Williams & Wilkins. Editors: Judith E. Thompson (pp. 277-290) (2009).
Sha. Ophthalmology. People's Military Medical Press. p. 138 (Apr. 30, 2013).
U.S. Appl. No. 18/119,251 Office Action dated Jul. 6, 2023.
Zhang. Modern Dermatologic Therapeutics. People's Military Medical Press p. 187 (May 31, 2022).
Bahn. The treatment of seborrheic blepharitis. South Med 47(8):749-53 (1954).
Chalmers et al. Contact Lens Dry Eye Questionnaire-8 (CLDEQ-8) and opinion of contact lens performance. Optom Vis Sci. 89:1435-1442 (2012).
Chalmers et al. Contact Lens Dry Eye Questionnaire-8 (CLDEQ-8): Use of an 8-Item Habitual Symptom Score to Reflect Change in Overall Opinion on Contact Lens Performance. Invest Ophthalmol Vis Sci 50:6337 (2009).
Chalmers et al. Cutoff score and responsiveness of the 8-item Contact Lens Dry Eye Questionnaire (CLDEQ-8) in a Large daily disposable contact lens registry. Cont. Lens. Anterior Eye. 39(5):342-52 (2016).
Charlton et al. Topical urea as a treatment for non-infectious keratopathy. Acta Ophthalmol Scand 74(4):391-394 (1996).
Cohen et al. Use of selsun in blepharitis marginalis. Am J Ophthalmol 38(4):560-562 (1954).
Efron et al. Lid Wiper Epitheliopathy. Prog Retin Eye Res. 53:140-174 (2016).
Foulks et al. The TFOS International Workshop on Contact Lens Discomfort: Report of the Subcommittee on Clinical Trial Design and Outcomes. Invest Ophthalmol Vis Sci 54:TFOS157-TFOS182 (2013).
Korb et al. Meibomian gland dysfunction and contact lens intolerance. J Am Optom Assoc 51(3):243-251 (1980).
Lavyel. Selsunef ointment to treat squamous blepharitis. Am J Ophthalmol 49:820-821 (1960).
Lindsley et al. Interventions for chronic blepharitis. Cochran Database Syst Rev 2012(5):CD005556 (2012).
Nichols et al. Dual-Polymer Drops, Contact Lens Comfort, and Lid Wiper Epitheliopathy. Optom Vis Sci. 93(8):979-86 (2016).
Nichols et al. The Performance of the Contact Lens Dry Eye Questionnaire as a Screening Survey for Contact Lens-related Dry Eye. Cornea 21(5):469-475 (2002).
Omali et al. Quantification of individual proteins in silicone hydrogel contact lens deposits. Mol Vis. 19:390-399 (2013).
PCT/IB2020/000262 International Search Report and Written Opinion dated Aug. 12, 2020.
Post et al. Demodex Folliculorum and Blepharitis Arch. Dermatol. 88(3):298-302 (1963).
Siddireddy et al. Predictive Potential of Eyelids and Tear Film in Determining Symptoms in Contact Lens Wearers. Optom Vis Sci 95(11):1035-1045 (2018).
Thygeson et al. Seborrheic blepharitis. Trans Am Ophthalmol Soc. 52:173-88 (1954-1955).
U.S. Appl. No. 17/357,749 Office Action dated Nov. 1, 2021.
U.S. Appl. No. 17/723,090 Office Action dated May 8, 2023.
Willis et al. Meibomian gland function, lid wiper epitheliopathy, and dry eye symptoms. Investigative Ophthalmology & Visual Science 52(14):3740-3740 (2011).
Young et al. Soft contact lens-related dryness with and without clinical signs. Optom. Vis. Sci. 89:1125-32 (2012).

SELENIUM DISULFIDE COMPOSITIONS FOR USE IN TREATING MEIBOMIAN GLAND DYSFUNCTION

CROSS REFERENCE

This application is a continuation of U.S. patent application Ser. No. 16/093,615, filed Oct. 12, 2018, which is the U.S. National Stage Patent Application of International Patent Application No. PCT/IB2017/000542, filed Apr. 13, 2017, which claims the benefit of U.S. Provisional Application No. 62/322,627, filed Apr. 14, 2016, all of which are incorporated herein by reference in their entirety.

BACKGROUND OF THE INVENTION

Meibomian gland dysfunction (MGD) is a leading contributor to dry eye syndrome and is often characterized by keratin-based obstruction of the gland, reduction in meibum quantity and quality, and increased viscosity of lipids produced by meibomian glands. Described herein are anhydrous selenium disulfide formulations which are chemically and physically stable, substantially free of aggregates, and substantially free of surfactants and dispersing agents. Such formulations show minimal diffusion onto the ocular surface. Also provided are methods for use of the formulations in the treatment of meibomian gland dysfunction.

SUMMARY OF THE INVENTION

One embodiment provides a composition for treating meibomian gland dysfunction comprising selenium disulfide and an anhydrous semi-solid ophthalmic base, wherein the composition is substantially free of selenium disulfide agglomerates, wherein the composition is substantially free of surfactants and dispersing agents, and wherein the composition is suitable for topical administration on the eyelid margin.

Another embodiment provides the composition wherein the selenium disulfide is dispersed in the anhydrous semi-solid ophthalmic base.

Another embodiment provides the composition wherein the anhydrous semi-solid ophthalmic base is an oleaginous base. Another embodiment provides the composition wherein the oleaginous base is selected from a group consisting of petroleum, white petroleum, and vegetable oils. Another embodiment provides the composition wherein the oleaginous base is selected from a group consisting of petroleum, white petroleum, mineral oil, vegetable oils and combinations thereof.

Another embodiment provides the composition wherein the anhydrous semi-solid ophthalmic base is prepared for use as a lip balm-like or stick formulation.

Another embodiment provides the composition wherein the composition has a melting point between about 34° C. and about 50° C.

Another embodiment provides the composition further comprising degradants of selenium disulfide, and wherein the amount of the degradants does not increase during a storage period, under accelerated stability conditions, at a temperature of about 40° C. Another embodiment provides the composition further comprising small amounts of degradants of selenium disulfide, and wherein the amount of the degradants does not increase above 1% of the total weight of the composition.

Another embodiment provides the composition wherein the composition exhibits no substantial color change, upon exposure to a temperature of about 60° C. for a period of time, and wherein the color change is determined by a colorimetric assay.

Another embodiment provides the composition wherein the composition further comprises squalene.

Another embodiment provides the composition wherein the composition further comprises hydrogenated oil.

Another embodiment provides the composition wherein the composition being substantially free of selenium disulfide agglomerates is an ointment/semi-solid defined as having an average selenium disulfide particle diameter of less than about 50 μm.

Another embodiment provides the composition wherein a composition being substantially free of selenium disulfide agglomerates is an ointment/semi-solid defined as having an average selenium disulfide particle diameter of about 5 μm and about 10 μm.

One embodiment provides a method for treating meibomian gland dysfunction in a patient in need thereof, comprising topically administering to the eyelid margin of the patient a composition comprising selenium disulfide and an anhydrous semi-solid ophthalmic base, wherein the composition is substantially free of selenium disulfide agglomerates, and wherein the composition is substantially free of surfactants and dispersing agents.

Another embodiment provides the method wherein the selenium disulfide is dispersed in the anhydrous semi-solid ophthalmic base. Another embodiment provides the method wherein the anhydrous semi-solid ophthalmic base is an oleaginous base. Another embodiment provides the method wherein the oleaginous base is selected from the group consisting of petroleum, white petroleum, and vegetable shortenings. Another embodiment provides the composition wherein the oleaginous base is selected from a group consisting of petroleum, white petroleum, mineral oil, vegetable oils and combinations thereof.

Another embodiment provides the method wherein the composition for topical administration has a melting point between about 34° C. and about 50° C.

Another embodiment provides the method wherein the composition for topical administration is stable under accelerated stability conditions, at a temperature of about 40° C.

Another embodiment provides the method wherein the composition for topical administration further comprises degradants of selenium disulfide, and wherein the amount of the degradants does not increase during a storage period, under accelerated stability conditions, at a temperature of about 40° C. Another embodiment provides the composition further comprising small amounts of degradants of selenium disulfide, and wherein the amount of the degradants does not increase above 1% of the total weight of the composition.

Another embodiment provides the method wherein the composition for topical administration exhibits no substantial color change, upon exposure to a temperature of about 60° C. for a period of time, and wherein the color change is determined by a colorimetric assay.

Another embodiment provides the method wherein the composition for topical administration further comprises squalene.

Another embodiment provides the method wherein the composition for topical administration is an ointment.

Another embodiment provides the method wherein the meibomian gland dysfunction is characterized by obstruction of meibomian gland.

Another embodiment provides the method wherein topical administration of the composition comprising selenium disulfide and an anhydrous ophthalmic base occurs until the meibomian gland obstruction is substantially removed.

Another embodiment provides the method wherein topical administration of the composition comprising selenium disulfide and an anhydrous ophthalmic base occurs periodically after removal of the meibomian gland obstruction, to prevent formation of a new meibomian gland obstruction.

Another embodiment provides the method wherein the composition being substantially free of selenium disulfide agglomerates is defined as a composition having an average selenium disulfide particle diameter of less than about 50 μm.

Another embodiment provides the method wherein the composition being substantially free of selenium disulfide agglomerates is defined as a composition having an average selenium disulfide particle diameter of between about 5 μm and about 10 μm.

One embodiment provides a method for treating meibomian gland dysfunction in a patient in need thereof, comprising topically administering to the eyelid margin of the patient a composition consisting of selenium disulfide and an anhydrous semi-solid ophthalmic base, wherein the composition is substantially free of selenium disulfide agglomerates, wherein the composition is substantially free of surfactants and dispersing agents, wherein the meibomian gland dysfunction is characterized by obstruction of meibomian gland and increased viscosity of meibum, and wherein the method results in substantial removal of the meibomian gland obstruction.

BRIEF DESCRIPTION OF THE FIGURES

FIG. 1 illustrates microscopic images of various selenium disulfide formulations in aqueous media.

FIG. 2 illustrates microscopic images of anhydrous selenium disulfide formulations.

DETAILED DESCRIPTION OF THE INVENTION

Described herein are compositions useful for treating meibomian gland dysfunction. Said compositions comprise anhydrous selenium disulfide ($SeS_2$) wherein the $SeS_2$ is dispersed in an anhydrous vehicle in a non-aggregated manner and the dispersion of $SeS_2$ is stable physically and chemically without use of surfactants, suspending agents or dispersing agents.

Figure 1A:
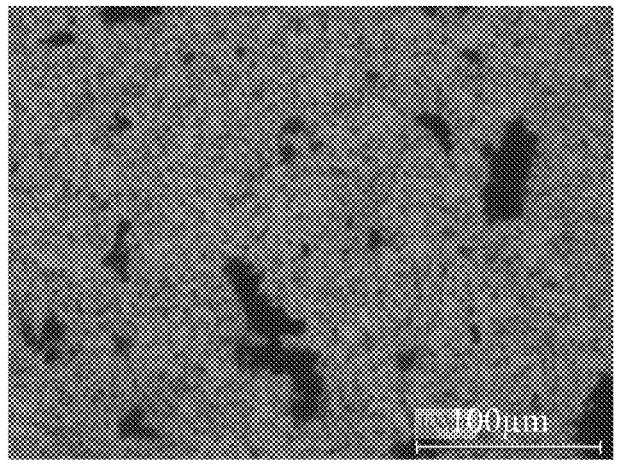
FIG. 1A, FIG. 1B, and FIG. 1C correspond to microscopic images of a Sebosel™ formulation, at 200× magnification, a dispersion of selenium disulfide in water at room temperature, at 100× magnification, and a 2.5% selenium disulfide formulation in Carbopol™ gel magnification at 100× magnification, respectively.
Figure 1B:
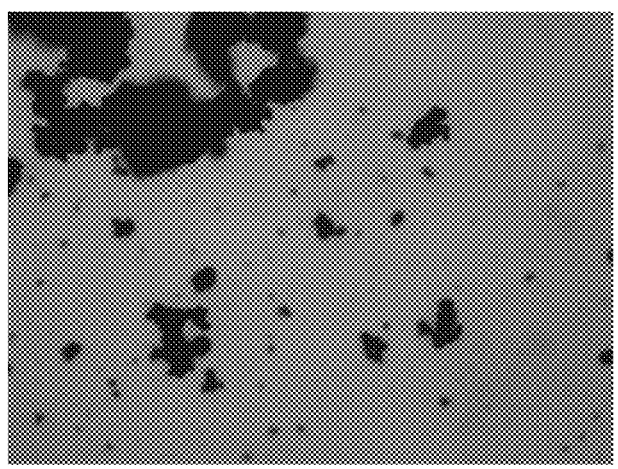
Figure 1C:
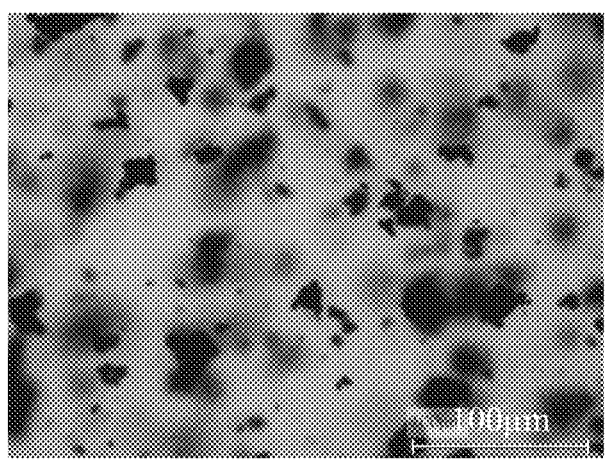

Contacting $SeS_2$ with aqueous medium causes immediate and spontaneous aggregation, such that $SeS_2$ particles with an average size of 5 to 10 microns will form large aggregates of 50 to 500 microns average size. $SeS_2$ in marketed products (e.g., Sebosel™) is present in such aggregates (FIG. 1). Surfactants and various suspending agents are required to stabilize $SeS_2$ suspension in liquid and semi-solid dosage forms in order to enable its topical application.

Unexpectedly, we have been able to achieve a stable suspension of $SeS_2$ by using an anhydrous semi-solid dosage forms without the use of surfactants or suspending agents. Additionally, the dispersion is substantially free of large aggregates and the suspended $SeS_2$ particles are evenly and homogeneously dispersed and distributed and therefore a high content uniformity is obtained.

Moreover, $SeS_2$ tends to degrade over time upon prolonged storage, and the degradation products have undesirable properties, such as increased toxicity. The developed suspension of $SeS_2$ has extremely improved chemical stability compared to currently marketed products. This improved stability is particularly important for ophthalmic applications since the ocular surface is more sensitive than the skin to $SeS_2$ degradation products. It has been observed that $SeS_2$ aqueous suspensions change color from orange to brown/gray colors at accelerated temperature conditions. Such discoloration indicates chemical degradation of the $SeS_2$ cyclic ring structure. The anhydrous and surfactant free formulation of $SeS_2$ disclosed herein does not degrade at the rate of the currently available $SeS_2$ compositions and is therefore much more suitable for ophthalmic use.

Previously Tseng described (US 2007/0082017) an ointment comprising a lipid composition to treat dry eye by applying the ointment to the inferior lid margin and by allowing diffusion of the lipid composition to the eye to integrate into tear film. However, in order to achieve sustained release of the ointment and to prevent a blurring of vision by the ointment by good dispersion tear fluid, Tseng is using a surfactant. The present invention relates to a composition applying to the eyelid having no surfactant. In the absence of surfactant, the present formulation tends to mix much less with tear fluid.

Stable Anhydrous Selenium Disulfide Formulations

Described herein in some embodiments are stable anhydrous formulations of selenium disulfide which are chemically stable, substantially free of aggregates and agglomerates. In some embodiments, the stable anhydrous selenium sulfide formulations described herein are substantially free of surfactants. In some embodiments, the stable anhydrous selenium sulfide formulations described herein are substantially free of dispersing agents. In some embodiments, the stable anhydrous selenium disulfide formulations described herein, contain about 0.05% to about 5% selenium disulfide. In some embodiments, the stable anhydrous selenium disulfide formulations described herein, contain about 2.5% selenium disulfide. In some embodiments, the stable anhydrous selenium disulfide formulations described herein, contain about 0.01% to about 10% selenium disulfide. In some embodiments, the stable anhydrous selenium disulfide formulations described herein, contain about 0.01% selenium disulfide. In some embodiments, the stable anhydrous selenium disulfide formulations described herein, contain about 0.05% selenium disulfide. In some embodiments, the stable anhydrous selenium disulfide formulations described herein, contain about 0.1% selenium disulfide. In some embodiments, the stable anhydrous selenium disulfide formulations described herein, contain about 0.5% selenium disulfide. In some embodiments, the stable anhydrous selenium disulfide formulations described herein, contain about 1.0% selenium disulfide. In some embodiments, the stable anhydrous selenium disulfide formulations described herein, contain about 1.5% selenium disulfide. In some embodiments, the stable anhydrous selenium disulfide formulations described herein, contain about 2.0% selenium disulfide. In some embodiments, the stable anhydrous selenium disulfide formulations described herein, contain about 2.5% selenium disulfide. In some embodiments, the stable anhydrous selenium disulfide formulations described herein, contain about 3.0% selenium disulfide. In some embodiments, the stable anhydrous selenium disulfide formulations described herein, contain about 3.5% selenium disulfide. In some embodiments, the stable anhydrous selenium disulfide formulations described herein, contain about 4.0% selenium disulfide. In some embodiments, the stable anhydrous selenium disulfide formulations described herein, contain about 4.5% selenium disulfide. In some embodiments, the stable anhydrous selenium disulfide formulations described herein, contain about 5.0% selenium disulfide. In some embodiments, the stable anhydrous selenium disulfide formulations described herein, contain about 5.5% selenium disulfide. In some embodiments, the stable anhydrous selenium disulfide formulations described herein, contain about 6.0% selenium disulfide. In some embodiments, the stable anhydrous selenium disulfide formulations described herein, contain about 6.5% selenium disulfide. In some embodiments, the stable anhydrous selenium disulfide formulations described herein, contain about 7.0% selenium disulfide. In some embodiments, the stable anhydrous selenium disulfide formulations described herein, contain about 7.5% selenium disulfide. In some embodiments, the stable anhydrous selenium disulfide formulations described herein, contain about 8.0% selenium disulfide. In some embodiments, the stable anhydrous selenium disulfide formulations described herein, contain about 8.5% selenium disulfide. In some embodiments, the stable anhydrous selenium disulfide formulations described herein, contain about 9.0% selenium disulfide. In some embodiments, the stable anhydrous selenium disulfide formulations described herein, contain about 9.5% selenium disulfide. In some embodiments, the stable anhydrous selenium disulfide formulations described herein, contain about 10.0% selenium disulfide.

In some embodiments, the anhydrous semi-solid base is an oleaginous base. Exemplary oleaginous bases, for the stable anhydrous selenium disulfide formulations described herein include petroleum base, mineral oil, a mixture of mineral oil and white petroleum, vegetable oil, or petroleum jelly (Vaseline®). In some embodiments, the vegetable oil is chosen from coconut oil, fractionated coconut oil, jojoba oil, olive oil, sunflower oil, almond oil, cod liver oil, castor oil or virgin wax In some embodiments, the stable anhydrous selenium disulfide formulations further comprise an oil. In some embodiments, the oil is chosen from a triglycerides, diglyceride, monoglycerides, acetylated lanolin alcohol, alkyl benzoate, an alkyl octanoate, almond oil, an unsaturated or polyunsaturated oil, apricot stone oil, arachidyl behenate, arachidyl propionate, avocado oil, barley oil, basil oil, beeswax, benzyl laurate, benzyl myristate, benzyl palmitate, bis (octyldodecyl stearoyl) dimer dilinoleate, borage seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, caprylyl methicone, cardamom oil, carrot oil, castor oil, cetearyl ethylhexanoate, cetearyl isononanoate, cetearyl octanoate, cetyl acetate, cetyl dimethicone, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cyclohexasiloxane, cyclomethicone, cyclomethicone 5-NF (cyclopentasiloxane), cyclotetrasiloxane, cypress oil, decyl oleate, diethyleneglycol, diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dimethicone, dimethyl polysiloxane, dioctyl malate, dioctyl sebacate, disopropyl adipate, dodecyl oleate, cyclotetrasiloxane (Dow Corning 244 Fluid), cyclohexasiloxane/cyclopentasiloxane (Dow corning 246 Fluid (d6+ d5)), epoxy-modified silicone oil, ester derivatives of lanolic acid, ethylhexyl cocoate, ethylhexyl ethylhexanoate, ethylhexyl hydroxystarate, ethylhexyl isononanoate, ethylhexyl palmitate, ethylhexyl palmytate, ethylhexyl pelargonate, ethylhexyl stearate, evening primrose oil, fatty acid-modified silicone oil, flaxseed oil, fluoro group-modified silicone oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hazelnut oil, heavy mineral oil, hempseed oil, herring oil, hexadecyl stearate, hexyl laurate, hydrocarbon oils, hydrogenated castor oil, hyssop oil, isoamyl laurate, isocetearyl octanoate, isocetyl isocetyl behenate, isocetyl lanolate, isocetyl palmitate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffin, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil, lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, methylphenylpolysiloxane, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, dimethiconol, palm oil, passionflower oil, peanut oil, rapeseed oil, rosehip oil, rye oil, safflower oil, sage oil, salmon oil, sesame oil, shea butter, silicone oils, soya oil, soybean oil, stearyl caprate, stearyl dimethicone, stearyl heptanoate, stearyl propionate, sunflower oil, sweet almond oil, synthetic isoalkane, sysymbrium oil, syzigium aromaticum oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, verbena oil, walnut oil, wheat germ glycerides, wheat germ oil, white petrolatum and mixtures thereof.

In some embodiments, the stable anhydrous selenium disulfide formulations described herein further comprise an oil chosen from caprylic acid triglyceride, isopropyl palmitate and isopropylpalmitate. In some embodiments, the stable anhydrous selenium disulfide formulations described herein further comprise caprylic acid triglyceride. In some embodiments, the stable anhydrous selenium disulfide formulations described herein further comprise mineral oil.

In some embodiments, the amount of mineral oil in the stable anhydrous selenium disulfide formulations described herein ranges from about 10% to about 97.5%. In some embodiments, the amount of caprylic acid triglyceride in the stable anhydrous selenium disulfide formulations described herein ranges from about 5% to about 50%.

In some embodiments, the amount of vaseline in the stable anhydrous selenium disulfide formulations described herein ranges from about 10% to about 97.5%. In some embodiments, the amount of waxes in the stable anhydrous selenium disulfide formulations described herein ranges from about 5% to about 50%.

In some embodiments, the stable anhydrous selenium disulfide formulations described herein, further comprise a silicone based excipient. In some embodiments, the silicone based excipient is chosen from dimethiconol, dimethicone, cyclopentasiloxane, decamethylcyclopentasiloxane, alkylmethyl siloxane copolyol, alkylmethyl siloxane and stearyltrimethylsilane or any silicone excipient blend suitable for the stable anhydrous selenium disulfide formulations according to the embodiments provided herein. In some embodiments, the silicone based excipient is dimethicone. In some embodiments, the silicone based excipient is stearyltrimethylsilane and stearyl alcohol.

In some embodiments, the stable anhydrous selenium disulfide formulations described herein further comprise a cellulose-derived solidifying agent. In some embodiments the cellulose-derived solidifying agent is microfibrillated cellulose. In some embodiments the cellulose-derived solidifying agent is nanocrystalline cellulose.

In some embodiments, the stable anhydrous selenium disulfide formulations described herein, further comprise a solidifying agent such as fumed silica, hydrogenated vegetable oils or waxes. In some embodiments, the fumed silica is Aerosil® fumed silica.

In some embodiments, the stable anhydrous selenium disulfide formulations described herein, further comprise squalene or squalane.

In some embodiments, the amount of squalene in the stable anhydrous selenium disulfide formulations described herein ranges from about 10% to about 97.5%. In some embodiments, the amount of squalene in the stable anhydrous selenium disulfide formulations described herein ranges from about 5% to about 30%.

Preventing leakage of selenium disulfide from the eye lids to the ocular surface is not desirable since its target organ, the meibomian gland and it orifices can only be reached from the lid edge and thus any spillage of the drug into the fornix' and onto the ocular surface reduces its effectiveness. Furthermore, avoiding leakage of selenium disulfide onto the aqueous ocular surface is desired so it does not aggregate and create large particles that can cause discomfort. In some embodiments the formulation has a specific melting point to allow stable and persistent presence of the ointment over the eyelid with minimal leak onto the ocular surface, yet, enables its penetration to the meibomian orifices, as well as liquefaction of the natural meibum lipids. Described herein in some embodiments is an ointment composition which is semi-solid at room temperature and has melting temperature between 33° C. to 36° C. In some embodiments is provided an ointment composition which is semi-solid at room temperature and has melting temperature between 33° C. to 46° C. In some embodiments is provided an ointment composition which is semi-solid at room temperature and has melting temperature between 33° C. to 38° C. In some embodiments is provided an ointment composition which is semi-solid at room temperature and has melting temperature between 33° C. to 40° C. In some embodiments is provided an ointment composition which is semi-solid at room temperature and has melting temperature between 33° C. to 42° C. In some embodiments is provided an ointment composition which is semi-solid at room temperature and has melting temperature between 33° C. to 44° C. In some embodiments is provided an ointment composition which is semi-solid at room temperature and has melting temperature between 34° C. to 37° C. In some embodiments is provided an ointment composition which is semi-solid at room temperature and has melting temperature between 35° C. to 38° C. In some embodiments is provided an ointment composition which is semi-solid at room temperature and has melting temperature between 32° C. to 40° C. In some embodiments is provided an ointment composition which is semi-solid at room temperature and has melting temperature between 33° C. to 56° C., wherein the composition releases squalene or other liquid lipids upon contact with eyelid margin. In some embodiments the formulation has a melting point that is higher than the temperature of the ocular surface which is about 34° C. so it does not liquefy when it comes in contact with the ocular surface but below 37° C. so it can penetrate the meibomian gland orifices.

Thin Layer of Drug Over Lid Margin

Lipid ophthalmic drug formulations are typically not well tolerated by patients since they get mixed into the tear fluid and cause blurred vision and also stick to the eye lashes and cause unpleasant sensation. It is therefore desired to provide a formulation that will not cause either of these side effects. In one embodiment of the present invention the formulation has viscosity characteristics that cause it to spread over the lid margin at a thickness of between 25 and 200 microns and preferably around 100 microns to allow enough drug to be in contact with the meibomian gland orifices while not creating a surplus of drug that would mix with the tear firm or stick to the eye lashes.

Agglomeration and Ophthalmic Compositions

Major problems related to ophthalmic compositions are crystallization and agglomeration of active ingredients during preparation as well as during storage. Crystallization or agglomeration of active pharmaceutical ingredient (API) leads to non-uniformity of dose, difficulty of administration, irritation to eye due to large drug particles and/or any ocular adverse effect due to high drug concentration or failure of treatment due to low drug concentration. Where the ophthalmic formulations are prepared as suspension, it is desirable to prepare the suspension in a manner such that the suspended particles do not agglomerate into larger ones upon storage. A particle size above 10 μm in diameter in an ophthalmic composition may result in a foreign body sensation in the eye following ocular application, causing reflex tearing. A reduction in particle size generally improves the patient comfort and acceptability of ophthalmic formulations. In addition, reduced particle size will increase the contact area between the selenium disulfide particles and the orifice of the meibomian gland thus increasing the effectiveness of the formulation.

Selenium disulfide forms agglomerates under aqueous conditions. Contacting selenium disulfide with aqueous medium causes immediate and spontaneous aggregation, causing selenium disulfide particles, with an initial average diameter of 5 to 10 μm, to aggregate into large clumps of 50 to 500 μm average diameter.

In some embodiments, the stable anhydrous selenium disulfide formulations described herein are substantially free of agglomerates. In some embodiments, substantially free of agglomerates means that the average selenium disulfide particle diameter throughout the formulation is less than about 50 µm, less than about 45 µm, less than about 40 µm, less than about 35 µm, less than about 30 µm, less than about 25 µm, less than about 20 µm, less than about 15 µm, less than about 10 µm, less than about 9 µm, less than about 8 µm, less than about 7 µm, less than about 6 µm, or less than about 5 µm. In some embodiments, substantially free of agglomerates means that the average selenium disulfide particle diameter throughout the formulation is no more than about 50 µm, no more than about 45 µm, no more than about 40 µm, no more than about 35 µm, no more than about 30 µm, no more than about 25 µm, no more than about 20 µm, no more than about 15 µm, no more than about 10 µm, no more than about 9 µm, no more than about 8 µm, no more than about 7 µm, no more than about 6 µm, or no more than about 5 µm. In some embodiments, substantially free of agglomerates means that the average selenium disulfide particle diameter throughout the formulation is between about 5 µm and about 10 µm, or between about 5 µm and about 15 µm, or between about 10 µm and about 20 µm, or between about 5 µm and about 20 µm, or between about 15 µm and about 25 µm. In some embodiments, substantially free of agglomerates means that the formulation contains less than about 10%, less than about 9%, less than about 8%, less than about 7%, less than about 6%, less than about 5%, less than about 4%, less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.5%, less than about 0.4%, less than about 0.3%, less than about 0.2%, or less than about 0.1% of agglomerates. In some embodiments, substantially free of agglomerates means that the selenium disulfide particle diameter increases no more than 10 times, no more than 9 times, no more than 8 times, no more than 7 times, no more than 6 times, no more than 5 times, no more than 4 times, no more than 3 times, no more than 2 times, or no more than 1.5 times upon formulation compared with the initial particle diameter.

In some embodiments, substantially free of agglomerate means that the formulation does not contains any selenium disulfide agglomerate. In some embodiments, the stable anhydrous selenium disulfide formulations described herein do not contain particles larger than 5 µm in diameter. In some embodiments, the stable anhydrous selenium disulfide formulations described herein do not contain particles larger than 10 µm in diameter. In some embodiments, the stable anhydrous selenium disulfide formulations described herein do not contain particles larger than 20 µm in diameter. In some embodiments, the stable anhydrous selenium disulfide formulations described herein do not contain particles larger than 10 µm in diameter and do not contain any surfactants and dispersing agents. In some embodiments, the stable anhydrous selenium disulfide formulations described herein is substantially free of surfactants and dispersing agents. In some embodiments, substantially free of surfactants and dispersing agents means that the formulation contains less than about 10% surfactants, dispersing agents, and combination thereof. In some embodiments, substantially free of surfactants and dispersing agents means that the formulation contains less than about 10%, less than about 9%, less than about 8%, less than about 7%, less than about 6%, less than about 5%, less than about 4%, less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.5%, less than about 0.4%, less than about 0.3%, less than about 0.2%, or less than about 0.1% surfactants, dispersing agents, and combination thereof. In some embodiments, substantially free of surfactants and dispersing agents means that the formulation contains no more than about 10% surfactants, dispersing agents, and combination thereof. In some embodiments, substantially free of surfactants and dispersing agents means that the formulation contains no more than about 10%, no more than about 9%, no more than about 8%, no more than about 7%, no more than about 6%, no more than about 5%, no more than about 4%, no more than about 3%, no more than about 2.5%, no more than about 2%, no more than about 1.5%, no more than about 1%, no more than about 0.9%, no more than about 0.8%, no more than about 0.7%, no more than about 0.6%, no more than about 0.5%, no more than about 0.5%, no more than about 0.4%, no more than about 0.3%, no more than about 0.2%, or no more than about 0.1% surfactants, dispersing agents, and combination thereof. In some embodiments, substantially free of surfactants and dispersing agents means that the formulation does not contains any surfactants, dispersing agents, and combination thereof. In some embodiments, substantially free of surfactants and dispersing agents means that the formulation is free of surfactants, dispersing agents, and combination thereof.

In some embodiments, the stable anhydrous selenium disulfide formulations described herein comprise a dispersion of selenium disulfide in an anhydrous semi-solid base. In some embodiments, the selenium sulfide is dispersed in the anhydrous base to form a homogenous dispersion without any large aggregates or clumps of particles. In some embodiments, the topical administration of a homogenous dispersion of selenium disulfide in an anhydrous semi-solid base, as described herein, to the eyelid margin of a patient, for treating meibomian gland dysfunction, does not cause any irritation to the eyes of the patient.

Chemical and Storage Stability of Selenium Disulfide Dispersion in Anhydrous Semi-Solid Ophthalmic Base Prior to the disclosures provided herein, surfactants and various suspending agents were required to stabilize selenium disulfide suspension in liquid and semi-solid dosage forms, and enable its topical application. The stable anhydrous selenium disulfide formulations described herein, in some embodiments, unexpectedly are stable without the use of surfactants or suspending agents or dispersing agents.

In some embodiments, the stable anhydrous selenium disulfide formulations described herein are physically stabilized against aggregation and chemically stabilized against degradation without the addition of surfactants, dispersing agents, or suspending agents.

In some embodiments, the stability of the formulations is tested under accelerated stability conditions, at a temperature between about of 40° C. and 60° C. for an extended storage period.

Stability of an ophthalmic formulation is determined by the extent of chemical degradation of the active ingredients via processes such as hydrolysis, oxidation, etc, during the period of storage.

Chemical Degradation is Characterized by Formation of Degradants

In some embodiments, the total amount of degradants in the stable anhydrous selenium disulfide formulations described herein does not increase over time during storage period. In some embodiments, the total amount of degradants in the stable anhydrous formulations described herein does not increase when the formulation is tested under accelerated stability conditions, at a temperature of about 40° C. and 60° C. and the degradation observed is lower in comparison to marketed $SeS_2$ drug products. Another embodiment provides the composition further comprising small amounts of degradants of selenium disulfide, and wherein the amount of the degradants does not increase above 1% of the total weight of the composition.

In some embodiments, the chemical stabilization of the stable anhydrous selenium disulfide formulations described herein is attributed to the reduced water content of the formulations. In some embodiments, the chemical stabilization of the stable anhydrous selenium disulfide formulations described herein is attributed to the anhydrous nature of the formulation. In some embodiments, the chemical stabilization of the stable anhydrous selenium disulfide formulations described herein is attributed to the lack of polyoxyethylene comprising stabilizing emulsifiers and dispersing agents in the formulation In some embodiments, drug instability in pharmaceutical formulations is detected by a change in the physical appearance, color, odor, taste, or texture of the formulation. In some embodiments, the stable anhydrous selenium disulfide formulations described herein do not exhibit any substantial change in color during a period of storage, under elevated temperatures. In some embodiments, the period of storage is two weeks at a temperature of about 60° C.

Melting Point of Stable Anhydrous Selenium Disulfide Formulations

In some embodiments, the stable anhydrous selenium disulfide formulations described herein has a melting temperature between about 34° C. and about 50° C. In some embodiments, the stable anhydrous selenium disulfide formulations described herein has a melting temperature of about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., or about 50° C. In some embodiments, the stable anhydrous selenium disulfide formulations described herein has a melting temperature close to and above the temperature of eyelid margin. In some embodiments, the melting point of the stable anhydrous selenium disulfide formulations described herein increases the bioavailability and efficacy of selenium disulfide.

Solid and Semi-Solid Dosage Form Composition Comprising Selenium Disulfide Dispersion in Anhydrous Semi-Solid Ophthalmic Base In some embodiments, the stable anhydrous selenium disulfide formulations described herein are part of a solid dosage form like a lip balm or a stick product, that is convenient to apply and spread over the eye lid margin in a similar manner to cosmetic eye lid product, whereas a very small amount of drug product is applied directly and precisely on the eye lid margin.

In some embodiments, the amount of drug product applied to the eye lid margin is about one mg. In other embodiments, the amount of drug product applied to the eye lid margin is less than 5 mg, less than 4 mg, less than 3 mg, or less than 2 mg.

In some embodiment, the stable anhydrous selenium disulfide composition comprises a synthetic or natural antioxidant selected from, for example, tocopherol or Vitamin E, EDTA (ethylenediamine tetraacetate), butylated hydroxyl anisole, butylated hydroxyl toluene, glutathione, astaxanthin, lutein, lycopene, propyl gallate, rosmarinic acid or ascorbyl palmitate.

In some embodiments, the stable anhydrous selenium disulfide formulations described herein are part of a semi-solid dosage form, such as an eye liner or a ointment product, that is convenient to apply and spread over the eye lid margin in a similar manner to cosmetic eye lid product, whereas a very small amount of drug product is applied directly and precisely on the eye lid margin.

Meibomian Gland

The meibomian glands are large sebaceous glands located in the eyelids, and unlike skin, are unassociated with hair. The meibomian glands produce the lipid layer of the tear film that protects it against evaporation of the aqueous phase. The meibomian gland orifice is located on the epithelial side of the lid margin, and is only a few hundred microns from the mucosal side. The glands are located on both upper and lower eyelids, with higher amounts of the glands on the upper eyelid. A single meibomian gland is composed of clusters of secretory acini that are arranged circularly around a long central duct and connected to it by short ductules. The terminal part of the central duct is lined by an ingrowth of the epidermis that covers the free lid margin and forms a short excretory duct that opens as an orifice at the posterior part of the lid margin just anterior to the mucocutaneous junction near the inner lid border. The oily secretion composed of lipids is synthesized within the secretory acini. The lipid secretion is a liquid at near body temperature and is delivered to the skin of the lid margin as a clear fluid, called "meibum." It forms shallow reservoirs on the upper and lower lid margins, and consists of a complex mixture of cholesterol, wax, cholesteryl esters, phospholipids, with small amounts of triglycerides, triacylglycerols, and hydrocarbons. The separate meibomian glands are arranged in parallel, and in a single row throughout the length of the tarsal plates in the upper and lower lids. The extent of the glands corresponds roughly to the dimensions of the tarsal plates.

Meibomian Gland Dysfunction (MGD)

The term, "meibomian gland dysfunction," as used herein, refers to chronic, diffuse abnormality of the meibomian glands that is characterized by terminal duct obstruction, or qualitative or quantitative changes in the glandular secretion, or both. MGD may result in alteration of the tear film viscosity, eye irritation symptoms, inflammation, or ocular surface disease. The most prominent aspects of MGD are obstruction of the meibomian gland orifices and terminal ducts and changes in the meibomian gland secretions.

MGD is a leading contributor of dry eye syndrome. The occurrence of dry eye syndrome is widespread and affects about 20 million patients in the United States alone. Dry eye syndrome is a disorder of the ocular surface resulting from either inadequate tear production or excessive evaporation of moisture from the surface of the eye. Tears are important to corneal health because the cornea does not contain blood vessels, and relies on tears to supply oxygen and nutrients. Tears and the tear film are composed of lipids, water, and mucus, and disruption of any of these can cause dry eye. MGD is not synonymous with posterior blepharitis, which describes inflammatory conditions of the posterior lid margin. MGD may cause posterior blepharitis, but MGD may not always be associated with inflammation or posterior blepharitis. MGD also refers to functional abnormalities of the meibomian gland, while "meibomian gland disease," describes a broad range of meibomian gland disorders, that includes neoplasia and congenital disease. Clinical signs of MGD include meibomian gland dropout, altered meibomian gland secretion, and changes in lid morphology.

Pharmaceutical Excipient

In other embodiments, the topical compositions described herein are combined with a pharmaceutically suitable or acceptable carrier (e.g., a pharmaceutically suitable (or acceptable) excipient, physiologically suitable (or acceptable) excipient, or physiologically suitable (or acceptable) carrier). Exemplary excipients are described, for example, in Remington: The Science and Practice of Pharmacy (Gennaro, 21$^{st}$ Ed. Mack Pub. Co., Easton, PA (2005)).

Methods of Treatment Utilizing Stable Anhydrous Selenium Disulfide Formulations

Described herein are methods for treating meibomian gland dysfunction in a patient in need comprising topical administration of a stable anhydrous selenium disulfide formulation to the eyelid margin of the patient in need. There are two potential categories of administration. One occurs with the assistance of a health-care provider: this category includes both acute and maintenance uses of the stable anhydrous selenium disulfide formulation. An acute use, in one embodiment, requires a stronger stable anhydrous selenium disulfide formulation (either in terms of concentration of the selenium disulfide or the inherent activity of the selenium disulfide). A maintenance use, in one embodiment, allows for the use of lower concentrations of the selenium disulfide, or selenium disulfide with lower inherent activity. A maintenance use, in one embodiment, involves a patient at a routine visit to the health care provider. Both acute uses and maintenance uses optionally involve use of an eye-protecting device or apparatus. In one embodiment, the acute use is performed by the health care provider, and the maintenance use is performed by the patient or non-health care provider. The second potential category of administration does not occur with the active assistance of a health care provider, but rather involves the patient applying the stable anhydrous selenium disulfide formulation to his/her eyelid margin. In one embodiment, such administration occurs over an extended period of time; one way of describing this patient-administered multi-administration mode is as a chronic use. In general, different or second formulations of the stable anhydrous selenium disulfide formulation are recommended for chronic or patient-administered uses. In one embodiment the different or second formulation utilizes a lower concentration of the stable anhydrous selenium disulfide formulation. In another embodiment, the second or different formulation utilizes a stable anhydrous selenium disulfide formulation that has a lower activity than the first formulation.

Provided herein is a method for treating meibomian gland dysfunction in a patient in need thereof, comprising topically administering to the patient a composition that reaches the eyelid margin of the patient, wherein the composition comprises a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

Provided herein is a method for treating meibomian gland dysfunction in a patient in need thereof, comprising topically administering to the patient a composition that reaches the eyelid margin of the patient, wherein the composition consists essentially of a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

It should be understood that the present methods also include the physical removal of the obstruction in the meibomian gland, followed by chronic and/or maintenance administration of the stable anhydrous selenium disulfide formulations described herein.

Provided herein is a method for removing a keratin obstruction from a meibomian gland in a patient in need thereof, comprising topically administering to the patient a composition that reaches the eyelid margin of the patient, wherein the composition comprises a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

Provided herein is a method for removing a keratin obstruction from a meibomian gland in a patient in need thereof, comprising topically administering to the patient a composition that reaches the eyelid margin of the patient, wherein the composition consists essentially of a therapeutically-effective amount of stable anhydrous selenium disulfide formulation. One embodiment provides the method wherein the concentration of the stable anhydrous selenium disulfide in the composition is between about 0.1% to about 10%. One embodiment provides the method wherein composition is topically administered to the patient until the keratinized obstruction is relieved. One embodiment provides the method wherein composition is topically administered to the patient periodically after relieving the keratinized obstruction. One embodiment provides the method wherein the topical administration is a single administration. One embodiment provides the method wherein the topical administration is a periodic administration. One embodiment provides the method wherein the periodic administration is once a day. One embodiment provides the method wherein the periodic administration is two times a day.

In some embodiments, topical administration of the composition comprising a selenium disulfide pharmacological agent and an anhydrous semi-solid ophthalmic base occurs twice a week. In some embodiments, topical administration of the composition comprising a selenium disulfide pharmacological agent and an anhydrous semi-solid ophthalmic base occurs every other day. In some embodiments, topical administration of the composition comprising a selenium disulfide pharmacological agent and an anhydrous semi-solid ophthalmic base occurs every day. In some embodiments, topical administration of the composition comprising a selenium disulfide pharmacological agent and an anhydrous semi-solid ophthalmic base occurs several times a day.

In some embodiments, the composition for topical administration is a liquid or a semi-solid. In some embodiments, the composition for topical administration is an emulsion semi-solid. In some embodiments, the composition for topical administration is a cream. In some embodiments, the composition for topical administration is an ointment. In some embodiments, meibomian gland opening pharmacological agent is suspended within the composition. In some embodiments, the composition for topical administration is a lotion. In some embodiments, the composition for topical administration is a gel. In some embodiments, the composition for topical administration is an anhydrous dispersion. In some embodiments, the composition for topical administration is an anhydrous lip balm or stick formulation or a device that enable the patient to target the eye lid margin.

One embodiment provides a method for treating a hyperkeratosis disorder in a patient in need thereof comprising topically administering to the eyelid margin of the patient a composition comprising a therapeutically-effective amount of a stable anhydrous selenium disulfide formulation, wherein the hyperkeratosis disorder is selected from meibomian gland dysfunction, or dry eye. Another embodiment provides the method wherein the hyperkeratosis disorder is meibomian gland dysfunction. Another embodiment provides the method wherein the hyperkeratosis disorder is dry eye.

One embodiment provides a method for removing a keratin obstruction of the meibomian gland in a patient having a hyperkeratosis disorder comprising topically administering to the eyelid margin of the patient a composition comprising a therapeutically-effective amount of a stable anhydrous selenium disulfide formulation, wherein the hyperkeratosis disorder is selected from meibomian gland dysfunction, or dry eye. Another embodiment provides the method wherein the hyperkeratosis disorder is meibomian gland dysfunction. Another embodiment provides the method wherein the hyperkeratosis disorder is dry eye.

One embodiment provides a method for treating an ophthalmic disorder caused by keratin obstruction of the meibomian gland in a patient in need thereof comprising topically administering to the eyelid margin of the patient a composition comprising a therapeutically-effective amount of a stable anhydrous selenium disulfide formulation, wherein the ophthalmic disorder is meibomian gland dysfunction or dry eye. Another embodiment provides the method wherein the ophthalmic disorder is meibomian gland dysfunction. Another embodiment provides the method wherein the ophthalmic disorder is dry eye.

Certain Definitions

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 10% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The terms "treat," "treating," or "treatment" as used herein, include reducing, alleviating, abating, ameliorating, relieving, or lessening the symptoms associated with MGD in either a chronic or acute therapeutic scenario. In one embodiment, treatment includes a reduction of a terminal duct obstruction.

The term "recurrence," or "reducing relapse" refers to return of MGD symptoms in a chronic therapeutic scenario.

The term "opening" refers to the clearing (at least in part) of an obstructed meibomian gland canal or orifice and/or maintaining the patency of the meibomian gland canal or orifice.

The term "anhydrous" as used herein refers to a composition containing less than 2% water by weight, or less than 1% water by weight, or a composition which does not contain any water.

The term "dispersion" as used herein refers to a system in which particles are dispersed in a continuous phase of a different composition or state. The dispersions are solid dispersions.

The term "agglomerates", "aggregates", and "clumps of particles" as used herein refers to a collection of particles. The terms are intended to be synonymous to each other and are used interchangeably.

The term "color stability" as used herein refers to the ability of a composition to substantially retain its original color during the time of storage. The term "substantially retain" means that there are no visually discernable changes in the color of the formulation over the time of storage or use.

The term "lotion" describes an emulsion liquid dosage form. This dosage form is generally for external application to the skin (US FDA Drug Nomenclature Monograph, number C-DRG-00201).

The term "cream" describes an emulsion semisolid dosage form, usually containing >20% water and volatiles and/or <50% hydrocarbons, waxes or polyols as the vehicle. A cream is more viscous than a lotion. This dosage form is generally for external application to the skin (US FDA Drug Nomenclature Monograph, number C-DRG-00201).

The term "ointment" describes a semisolid dosage form, usually containing <20% water and volatiles and/or >50% hydrocarbons, waxes or polyols as the vehicle. This dosage form is generally for external application to the skin or mucous membranes (US FDA Drug Nomenclature Monograph, number C-DRG-00201).

The term "solution" describes a clear, homogeneous liquid dosage form that contains one or more chemical substances dissolved in a solvent or mixture of mutually miscible solvents (US FDA Drug Nomenclature Monograph, number C-DRG-00201).

The term "suspension" refers to a heterogeneous mixture containing solid particles that are sufficiently large for sedimentation.

EXAMPLES

Example 1: Stable Anhydrous Selenium Disulfide Formulations

Several formulations of anhydrous selenium disulfide were prepared and the detailed compositions are listed in Table 1.

TABLE 1

Exemplary formulations of anhydrous selenium disulfide

| | Formulation | | | | | |
|---|---|---|---|---|---|---|
| Ingredients | FO2 % W/W | FS2 % W/W | FA1 % W/W | FM1 % W/W | FM2 % W/W | FM3 % W/W |
| Selenium disulfide | 2.5 | 2.5 | 2.5 | 2.5 | 2.5 | 2.5 |
| Mineral oil | 20 | — | 72.5 | 97.5 | — | 30 |
| Vaseline | 62.5 | 32.5 | — | — | 97.5 | 67.5 |
| Capric caprylic triglyceride | 10 | 10 | 20 | — | — | — |
| Dimethicone (Dow corning) | — | 40 | — | — | — | — |
| Wax 10 (Dow corning) | — | 10 | — | — | — | — |
| Squalane | 5 | 5 | — | — | — | — |
| Fumed silica Aerosil 200 | — | — | 5 | — | — | — |

Example 2: Dispersion of SeS$_2$ in Aqueous and Anhydrous Medium

Figure 2A:
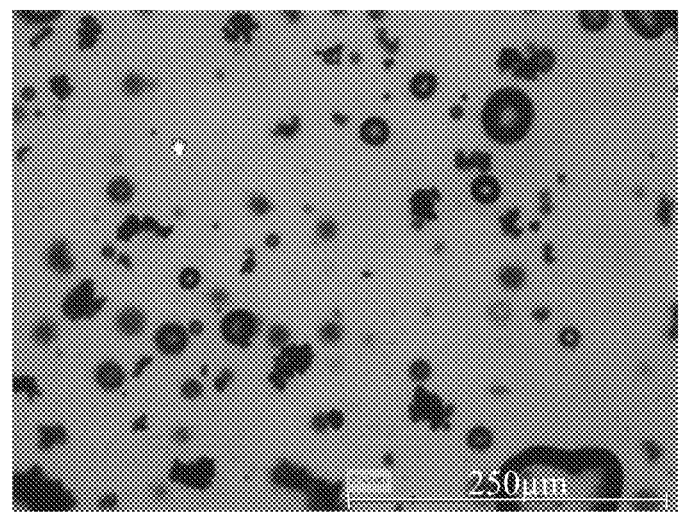
FIG. 2A and FIG. 2B correspond to microscopic image of anhydrous selenium disulfide formulation FO2 and FS2 respectively, at 100× magnification.
Figure 2B:
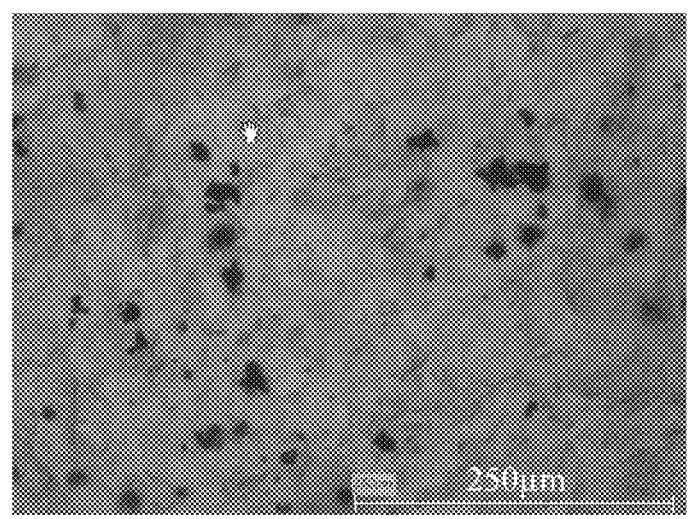

Microscopic images were acquired of Selenium disulfide dispersions in either aqueous mediums or anhydrous ointments, and Sebosel™ (containing 2.5% selenium disulfide). The aqueous dispersions of 2.5% selenium disulfide in water or Carbopol™ gel were found to form clumps or aggregates or agglomerates, as shown in FIGS. 1 A-C. In contrast, the selenium sulfide formulations FO2 and FS2, containing 2.5% selenium disulfide dispersed in anhydrous ointments were found to be smooth homogenous dispersions and did not contain any large clumps or aggregates or agglomerates, as shown in FIGS. 2 A-B.

Example 3: Anhydrous Selenium Disulfide Stability Study by Change of Color

Stability of an exemplary anhydrous selenium disulfide formulation, FO2, was tested by monitoring whether the formulation changed color during a storage period of two weeks at 60° C. As shown in Table 2, the FO2 formulation did not change color under the test conditions, whereas Sebosel™, which contains 2.5% selenium disulfide dispersed in an aqueous medium, changed color from orange to deep brown. The results indicate that the anhydrous selenium disulfide formulations described herein, have improved physical stability and improved shelf-life.

TABLE 2

Comparison of stability of anhydrous selenium disulfide and Sebosel ™

| Formulation | Color | 2 weeks 60° C. |
|---|---|---|
| Sebosel ™ | Orange | Deep brown |
| FO2 | Orange | Orange |

TABLE 3

Examples of semi solid and solid type anhydrous formulations of SeS$_2$

| | LBM29 % W/W | LBM35 % W/W | LBM36 % W/W | LBM37 % W/W | LBM38 % W/W |
|---|---|---|---|---|---|
| SeS$_2$ | 1 | 1 | 1 | 1 | 1 |
| Microcrystalline wax | | | | 10 | |
| Vaseline | 7 | 7 | 7 | 7 | 7 |
| Lanolin | 6 | 6 | 6 | 6 | 6 |
| Capric/caprylic triglycerides | 39 | 35.5 | 33 | 28 | 28 |
| Squalane | 39 | 35.5 | 33 | 28 | 28 |
| Hydrogenated Vegetable Oil | 8 | 15 | 20 | 20 | 30 |
| Total | 100 | 100 | 100 | 100 | 100 |

The formulations of Table 3, were placed in 40° C. and 60° C. stability chamber and show less change of color in comparison to marketed SeS$_2$ drug products, and with various melting point and spread ability and viscosity or hardness.

TABLE 4 examples of semi solid and solid type anhydrous formulations of SeS$_2$

|  | LBM53 % W/W | LBM59 % W/W | LBM60 % W/W | LBM61 % W/W | LBM63 % W/W | LBM64 % W/W | LBM65 % W/W | LBM66 % W/W |
|---|---|---|---|---|---|---|---|---|
| SeS2 | 0.5 | 0.5 | 0.5 | 0.5 | 0.5 | 0.5 | 0.5 | 0.5 |
| Microcristalline wax | 25 | 33 | 25 | 25 | 25 |  |  |  |
| Vaseline | 20.5 | 10.5 | 20.5 | 20.5 | 24 | 24 | 24 | 24 |
| Capric/caprylic acid (TCC) | 17 | 17 | 34 | 17 | 17 | 17 | 17 | 17 |
| Squalane | 17 | 17 |  | 12 | 7.9 | 7.9 | 7.9 | 7.9 |
| Mineral oil |  |  |  |  |  | 25 | 30 | 40 |
| Cutina HR PH (Hydrogenated castor oil) | 20 | 20 | 10 | 20 | 20 | 20 | 20 | 10 |
| Dermofeel viscolid |  |  | 10 |  | 5 | 5 |  |  |
| Dimethicone (Dow C.) |  | 2 |  |  |  |  |  |  |
| TPGS |  |  |  | 5 |  |  |  |  |
| Tocopherol |  |  |  |  | 0.5 | 0.5 | 0.5 | 0.5 |
| BHT |  |  |  |  | 0.1 | 0.1 | 0.1 | 0.1 |
| Total | 100 | 100 | 100 | 100 | 100 | 100 | 100 | 100 |
| Consistency 1 to 5 | 4 | 4 | 5 | 5 | 5 | 1 | 1 | 1 |
| Spreadability 1 to 5 | 4 | 3 | 5 | 5 | 5 | 1 | 1 | 1 |
| 60 C. few days | 5 | 5 | 3 | 3 | 5 | 5 | 5 | 5 |

*Score 1 to 5: 5 is the highest or best results and 1 is worst or low result

Formulations 53, 59, 60, 61 and 63 are hard and formulations 64, 65 and 66 are soft type. The hard formulations show better spread ability formulations 60 and 61 show some change of color at accelerated stability test at 60° C. whereas all other formulations did not changed color over a few days at 60° C. whereas Sebosel™ lost its typical orange color and became dark brown. Moreover, formulations 64, 65 and 66 did not change color over at least three weeks at 60° C. All formulations exhibited very fine and uniform dispersion of SeS$_2$ and no aggregation at regular and accelerated stability conditions. Formulations 53, 59, 60, 61 and 63 did not change color over at least one month at 40° C. Formulations 64, 65 and 66 did not change color over at least three months at 40° C.

Example 4: Destabilizing Inactive Ingredients

Formulations that contained inactive ingredients comprising polyethylene glycol moiety, such as tween or pluronic or tocopherol polyethyelene glycol or vinylpyrrolidone comprising molecules, reduced SeS$_2$ chemical stability and a black color was observed within two hours to two days upon storage at 60° C.

What is claimed is:

1. A composition comprising selenium disulfide and an anhydrous semi-solid ophthalmic base, wherein any selenium disulfide particles of the composition have an average diameter of less than 50 μm, wherein the composition comprises less than 10 % w/w of surfactants and dispersing agents, and wherein the composition is suitable for topical administration on an eyelid margin.

2. The composition of claim 1, wherein the selenium disulfide is dispersed in the anhydrous semi-solid ophthalmic base.

3. The composition of claim 1, wherein the anhydrous semi-solid ophthalmic base is an oleaginous base selected from the group consisting of petroleum, white petroleum, mineral oil, vegetable oils and combinations thereof.

4. The composition of claim 3, wherein the anhydrous semi-solid ophthalmic base is petroleum or mineral oil.

5. The composition of claim 1, wherein the composition is formulated as a spreadable lip balm-or stick-like product.

6. The composition of claim 1, wherein the composition or base thereof has a melting point between about 34° C. and about 50° C.

7. The composition of claim 1, wherein the composition further comprises squalene or hydrogenated oil.

8. The composition of claim 7, wherein the composition comprises 5 % w/w to 30 % w/w squalene.

9. The composition of claim 7, wherein the composition comprises 8 % w/w to 30 % w/w hydrogenated oil.

10. The composition of claim 1, wherein any disulfide agglomerates in the composition have a particle diameter of less than 20 μm.

11. The composition of claim 1, wherein any selenium disulfide particles of the composition have an average selenium disulfide particle diameter of less than about 20 μm.

12. The composition of claim 1, wherein any selenium disulfide particles of the composition have an average selenium disulfide particle diameter of about 5 μm to about 20 μm.

13. The composition of claim 1, wherein any selenium disulfide particles of the composition have an average selenium disulfide particle diameter of less than about 15 μm.

14. The composition of claim 1, wherein any selenium disulfide particles of the composition have an average selenium disulfide particle diameter of about 5 μm to about 10 μm.

15. The composition of claim 1, wherein the composition does not contain selenium disulfide particles larger than 20 μm in diameter.

16. The composition of claim 1, wherein the composition is substantially free of surfactants and dispersing agents.

17. The composition of claim 1, wherein the composition comprises less than 1 % w/w of surfactants and dispersing agents.

18. The composition of claim 1, further comprising degradants of selenium disulfide.

19. The composition of claim 18, wherein an amount of the degradants does not increase during a storage period, under accelerated stability conditions, at a temperature of 40° C.

20. The composition of claim 1, wherein the composition further comprises a small amount of degradants of selenium disulfide, wherein the amount of the degradants does not increase above 1% of the total weight of the composition.

21. The composition of claim 1, wherein the composition comprises selenium disulfide at a concentration of about 0.01 % w/w to about 10 % w/w.

22. The composition of claim 21, wherein the composition comprises selenium disulfide at a concentration of about 0.05 % w/w to about 5 % w/w.

23. The composition of claim 22, wherein the composition comprises selenium disulfide at a concentration of about 0.5 % w/w.

24. A method for treating meibomian gland dysfunction (MGD) in a patient in need thereof, the method comprising topically administering to the eyelid margin of the patient a therapeutically effective amount of the composition of claim 23.

25. A method for treating dry eye disease in a patient in need thereof, the method comprising topically administering to the eyelid margin of the patient a therapeutically effective amount of the composition of claim 23.

26. The composition of claim 22, wherein the composition comprises selenium disulfide at a concentration of about 1.0 % w/w.

27. A method for treating a hyperkeratosis disorder in a patient in need thereof, the method comprising topically administering to the eyelid margin of the patient a therapeutically effective amount of the composition of claim 1.

\* \* \* \* \*